United States Patent
Carr et al.

(10) Patent No.: US 9,341,559 B2
(45) Date of Patent: May 17, 2016

(54) METHOD AND APPARATUS FOR ANALYZING A SAMPLE OF SUB-MICRON PARTICLES

(75) Inventors: Robert Jeffrey Geddes Carr, Wiltshire (GB); John Patrick Hole, Wiltshire (GB); Jonathan Benjamin Kendall Smith, Wiltshire (GB)

(73) Assignee: Malvern Instruments Limited (GB)

( * ) Notice: Subject to any disclaimer, the term of this patent is extended or adjusted under 35 U.S.C. 154(b) by 0 days.

(21) Appl. No.: 14/235,988

(22) PCT Filed: Aug. 6, 2012

(86) PCT No.: PCT/GB2012/051899
§ 371 (c)(1),
(2), (4) Date: Jan. 29, 2014

(87) PCT Pub. No.: WO2013/021185
PCT Pub. Date: Feb. 14, 2013

(65) Prior Publication Data
US 2014/0152978 A1    Jun. 5, 2014

(30) Foreign Application Priority Data

Aug. 5, 2011 (GB) .................................. 1113542.3

(51) Int. Cl.
*G01N 15/02*   (2006.01)
*G01N 15/14*   (2006.01)
*G01N 15/00*   (2006.01)

(52) U.S. Cl.
CPC ............ *G01N 15/14* (2013.01); *G01N 15/0211* (2013.01); *G01N 15/1459* (2013.01);
(Continued)

(58) Field of Classification Search
CPC .............. G01N 15/14; G01N 15/0211; G01N 15/1459; G01N 2015/0038; G01N 2015/0238; G01N 2015/025; G01N 2015/0222; G01N 2015/0277

See application file for complete search history.

(56) References Cited

U.S. PATENT DOCUMENTS

2007/0104649 A1 * 5/2007 Fischer et al. ................. 424/9.6
2009/0251696 A1 * 10/2009 McNeil-Watson et al. ... 356/336
(Continued)

FOREIGN PATENT DOCUMENTS

CN    102109454 A    6/2011
WO    03/093801 A1   11/2003

OTHER PUBLICATIONS

Vasco Filipe et al: Critical Evaluation of Nanoparticle Tracking Analysis (NTA) by NanoSight for the Measurement of Nanoparticles and Protein Aggregates, Pharmaceutical Research, Kluwer Academic Publishers-Plenum Publishers, NL, vol. 27, No. 5, Mar. 4, 2010.

(Continued)

*Primary Examiner* — Tarifur Chowdhury
*Assistant Examiner* — Michael P Lapage
(74) *Attorney, Agent, or Firm* — Barnes & Thornburg LLP (57) ABSTRACT

The present invention provides a method of analyzing a sample comprising sub-micron particles, comprising determining first information about the size of particles and number of particles in the sample by nanoparticle tracking analysis; determining second information about average particle size of particles in the sample by dynamic light scattering; determining from the first information third information representing the theoretical effect of the detected particles on results obtainable by dynamic light scattering; and adjusting the second information using the third information to produce fourth information representing adjusted information on average particle size.

20 Claims, 5 Drawing Sheets

(52) U.S. Cl.
CPC .. *G01N2015/0038* (2013.01); *G01N 2015/025* (2013.01); *G01N 2015/0222* (2013.01); *G01N 2015/0238* (2013.01); *G01N 2015/0277* (2013.01)

(56) References Cited

U.S. PATENT DOCUMENTS

2009/0291430 A1\* 11/2009 Gabriel .............................. 435/5
2012/0198922 A1\* 8/2012 Maurer et al. ............... 73/61.41

OTHER PUBLICATIONS

Iker Montes-Burgos et al: "Characterisation of nanoparticle size and state prior to nanotoxicological studies", Journal of Nanoparticle Research ; An Interdisciplinary Forum for Nanoscale Science and Technology, Kluwer Academic Publishers. DO. vol. 12, No. 1, Oct. 13, 2009.

Robert D Boyd et al: "New approach to inter-technique comparisons for nanoparticle size measurements; using atomic force microscopy. nanoparticle tracking analysis and dynamic light scattering", Colloids and Surfaces. A, Physicachemical and Engineering Aspects, Elsevier, Amsterdam, NL, vol. 387, No. 1, Jul. 10, 2011.

Malloy A et al: "Nanoparticle tracking analysis—The halo(TM) system", Particle and Particle Systems Characterization, VCH, Weinheim, DE. vol. 23. No. 2, Aug. 1, 2006.

International Search Report and Written Opinion in PCT/GB2012/051899, Nov. 15, 2012.

\* cited by examiner

METHOD AND APPARATUS FOR ANALYZING A SAMPLE OF SUB-MICRON PARTICLES

This patent application is a U.S. nationalization under 35 USC §371 of International Application No. PCT/GB2012/051899, filed Aug. 6, 2012, which claims priority to Great Britain Patent Application No. 1113542.3, filed Aug. 5, 2011. The disclosures set forth in the referenced applications are incorporated herein by reference in their entireties

FIELD OF THE INVENTION

This invention relates to the optical detection and analysis of particles, particularly sub-micron particles including nanoparticles, i.e. particles typically having a major dimension of less than 100 μm, generally less than 50 μm.

BACKGROUND TO THE INVENTION

The analysis of nanoparticles is a ubiquitous requirement in a broad range of industry sectors. Product performance and stability frequently depends on the ability to manufacture particle suspensions to fine tolerances without the presence of contaminants or aggregates. Foremost in such analyses is particle size and size distribution measurement for which a number of techniques are well established and commonly employed in routine quality control as well as in a research and development environment. Depending on the nature of the product and the particle characteristics sought, one or more of a range of analytical methodologies are employed which include electron microscopy, dynamic light scattering (DLS), Fraunhofer scattering, single particle detection techniques, optical microscopy, etc. For particles in the nanoscale, however, only the first two of these examples are used frequently. While widespread, both have drawbacks including capital and running costs, analysis turnaround time, and, in the case of dynamic light scattering, a limited ability to resolve particle size distribution profiles.

Dynamic Light Scattering (DLS)

Dynamic light scattering techniques such as photon correlation spectroscopy (PCS) analyse a large ensemble of many thousands of particles from which only a z-average particle diameter, i.e. intensity weighted particle mean diameter, is obtained as well as a polydispersity quotient indicating the width of the particle size distribution (Pecora, R., (Ed)(1985) Dynamic Light Scattering, Applications of Photon Correlation Spectroscopy, Plenum Press, New York). The technique is typically practiced on a sample comprising a suspension of nanoparticles in a liquid, illuminated by a suitably focussed coherent, monochromatic laser beam of approximately 100 microns diameter, the light scattered from which is detected by a photon counting photomultiplier. The detector is configured, by means of a pinhole and slit combination or single mode fibre optic, to observe only a single coherence area or speckle from the light scattered by the sample into the far field. The intensity of light within the coherence area fluctuates through interference effects as a consequence of random Brownian motion of the nanoparticles and the characteristic timescale of the intensity fluctuations are analysed by a digital correlator. The average rate of change of the intensity fluctuations can be expressed in terms of particle diffusion coefficient ($D_t$) from which a sphere equivalent hydrodynamic diameter of particles in the path of the laser beam can be estimated. The maximum dimension, e.g. diameter, of particles as small as 2-3 nm can be determined in this way. However, as all particles are measured simultaneously in DLS, it is frequently the case that a relatively small number of highly scattering larger particles (e.g. contaminants or aggregates) can dominate the signal and effectively obscure the presence of the bulk of the smaller particles that may be present. In some limited circumstances it is possible, through the application of various de-convolution algorithms, to extract particle size distribution structure (e.g. a bimodal distribution) from the results obtained but this approach is reliable only if the two populations are not too polydisperse themselves or too close together in size. In practice, particles which differ in diameter by less than a ratio of 3 cannot normally be resolved. This represents a severe limitation in applications in which accurate information about particle size distribution is required, but the samples contain larger particles (e.g. contaminants or aggregates) which significantly bias the results and can partially or totally mask the presence of smaller particles. Equally, inherently complex polydisperse and heterogeneous samples containing a broad range of particle sizes generate distributions which are frequently badly skewed to the larger particle sizes present. Finally, being an ensemble technique, no direct information concerning the numbers of any particular particle size or size class can be recovered from DLS.

Nanoparticle Tracking Analysis (NTA)

Nanoparticle tracking analysis is a recently developed method for the direct and realtime visualisation and analysis of nanoparticles in liquids. See e.g. WO 03/093801. Based on a laser illuminated microscopical technique, Brownian motion of nanoparticles is analysed in real-time by a charge-couple device (CCD) camera, each particle being simultaneously but separately visualised and tracked by a dedicated particle tracking image-analysis programme. Because each particle is visualised and analysed separately, the resulting estimate of particle size and particle size distribution does not suffer from the limitation of being an intensity weighted, z-average distribution, which is the norm in conventional ensemble methods of particle sizing in this size regime, e.g. dynamic light scattering (DLS) as described above. The ability of NTA to measure simultaneously particle size and particle scattering intensity allows heterogeneous particle mixtures to be resolved and, importantly, particle concentration to be estimated directly, the particle size distribution profile obtained by NTA being a direct number/frequency distribution.

NTA has become a term of art, recognised by those skilled in the relevant field. There are over 250 scientific papers and presentations referring to data collected using NTA. Further the term is used by, for example, ASTM International (formerly the American Society for Testing and Materials), the Environmental Protection Agency (EPA), the Food and Drug Administration (FDA) and the NIH.

The range of particle sizes that can be analysed by NTA depends on the particle type. The lower size limit is defined by the particle size and particle refractive index given that sufficient light must be scattered by each particle for it to be detected and tracked as described above. For particles with very high refractive indices, such as colloidal gold, accurate determination of size can be achieved down to particles with a maximum dimension of about 10 nm. For lower refractive index particles, such as those of biological origin, the smallest detectable size might be in the range 25-50 nm Accordingly, NTA is limited by its ability to detect particles below a certain size.

With NTA, the presence and analysis of particles, each of which scatters sufficient light to be detected individually, can still be carried out even in the presence of 'background' material comprising, for instance, a population of very small particles (such as protein molecules, sub-10 nm inorganic material, polymer solutions, nano-emulsions, etc.) each of which is too small to detect individually but which is present in sufficiently high concentration to collectively form a background haze of scattered light. This background cannot be analysed by NTA but particles visible as discrete light scattering entities embedded within in this background may be analysed by NTA. Of course, the intensity of this background will determine the limit of sensitivity of NTA in terms of minimum detectable size. Further, NTA is able to identify, track and analyse suitably sized particles even when they are present in heterogeneous samples containing high numbers of larger particles.

NTA is further capable of detecting and analysing fluorescent or fluorescently labelled nanoparticles in the presence of a non-fluorescent background though use of appropriate fluorescence exciting optical sources and suitable fluorescence filters. NTA is further capable of measuring more than one fluorescence wavelength within a sample using multiple filters or a colour camera.

Thus, DLS can serve the requirements of analysis of nanoparticle size down to sizes of 2-3 nm but suffers badly from an intensity weighting to larger particles (such as contaminants or aggregates) in the sample and cannot furnish information about particle number, whereas NTA can detect, analyse and count individual particles down to sizes of, say, 10-50 nm but cannot detect and analyse particles below this size limit which, if present, appear as a background haze. NTA-detectable particles are referred to herein as relatively larger particles or contaminant particles, and smaller particles, not detectable by NTA, are referred to herein as relatively smaller particles, haze or background.

SUMMARY OF THE INVENTION

According to the present invention, there is provided a method of analysing a sample comprising sub-micron particles, comprising determining first information about the size of particles and number of particles in the sample by nanoparticle tracking analysis; determining second information about average particle size of particles in the sample by dynamic light scattering; determining from the first information third information representing the theoretical effect of the detected particles on results obtainable by dynamic light scattering; and adjusting the second information using the third information to produce fourth information representing adjusted information on average particle size.

The present invention is based on the discovery that information gained through NTA analysis about the size, relative light scattering intensity and number of individually detectable relatively large particles (contaminant particles) present in a background of non-optically resolvable nano-particulate material (haze) (the first information) can be used to modify and improve the results gained by DLS analysis of such a sample (the second information). We have shown that it is possible to use this data to model and thus estimate the contribution such relatively larger particles would make to a DLS measurement of such a sample (the third information), remove the effect of such particles on the DLS analysis and thus obtain the 'contaminant-corrected' DLS results (the fourth information). In this way, more accurate information can be obtained about the relatively smaller particles than has hitherto been possible.

The invention can thus obtain the benefit of DLS analysis of relatively smaller particles, but without the presence of relatively larger particles adversely affecting the accuracy of analysis of such relatively smaller particles as has hitherto been the case.

The invention is thus applicable to samples comprising particles with different sizes, especially a plurality of different sizes, and in particular including both relatively smaller particles having a maximum dimension less than about 10-50 nm, and relatively larger particles acting as contaminant.

The first and second information are preferably obtained from the same sample, simultaneously. However, for samples containing a sufficiently high number of particles in the measurement volume such that adjacent regions contain a statistically similar number of particles of similar particle size distribution, measurements of the first and second information may be obtained from different regions of the sample without accuracy being significantly adversely affected. In cases where the sample does not change significantly with time, the first and second information need not be obtained simultaneously, although this is not appropriate in cases where, say, the size of the particles changes with time, e.g. through aggregation, precipitation, dissolution, dispersion etc.

The sample will typically, but not necessarily, comprise a liquid comprising a suspension or other dispersion of particles. The particles may be solid or may conceivably be liquid (e.g. fine droplets in an emulsion). A liquid sample will normally, but not inevitably, be an aqueous liquid.

Convenient sample volumes are typically 500 µl or 250 µl, with the sample conveniently being contained in a suitable sample cell.

The sample is illuminated by a suitably focussed beam of radiation, typically a laser beam.

NTA may be carried out in generally conventional manner, e.g. as described in WO 03/093801.

The first information obtained by NTA, desirably includes information on particle brightness/spectral characteristics, as well as particle size and number.

DLS may be carried out in generally conventional manner, e.g. as described above.

The second information, obtained by DLS, includes information on average particle size in the form of z-average particle diameter, and optionally also includes information on particle size distribution.

NTA and DLS are typically carried out using respective detector systems, which may be of conventional construction and which each includes a suitable light detector, typically a CCD. It may, however, be possible to use a single CCD camera for both NTA and DLS measurements, provided the camera has a suitable efficiency and response rate for DLS. DLS conventionally may utilise a photon detector/multiplier, such as an Avalanche Photodiode (APD).

The first information is preferably used to generate a theoretical correlation curve or function ($g^2(\tau)$) for one or more of the detected particle sizes. The correlation functions are preferably size-weighted, with larger particles being given greater weighting. The correlation functions for different particle sizes, preferably size-weighted, may then be summed.

Desirably the first information includes information on the relative amount of light scattered by each detected particle, e.g. by summing the grey-scale values from CCD camera pixels imaging the spot of light scattered by each particle. This information can be used to estimate directly the degree to which each NTA-detected particle would contribute to the overall signal detected by DLS, to generate the third information.

The relatively smaller particles typically comprise proteins, with the sample also containing larger particles, e.g. contaminants, protein aggregates, etc.

The relatively larger (NTA-detectable) particles may be biological in nature, e.g. being macromolecules such as DNA or supramolecular constructs such as viruses. The relatively larger particles may alternatively comprise engineered nanoparticles.

In one embodiment, the sample comprises cell cytosol (constituting relatively smaller, PCS-measurable background particles) and relatively larger particles e.g. engineered nanoparticles.

The particles, particularly the relatively larger particles, may be fluorescent or may be labelled with one or more fluorescent moieties, possibly using a number of different fluorescent moieties with different fluorescence characteristics that can be distinguished spectrally and spatially.

NTA data on larger particles may be used to allow changes (or otherwise) in the relative amount or concentration of PCS-measurable material to be monitored.

The sample may be such that larger NTA-detectable particles appear and grow in size through aggregation or precipitation of the background material and which can therefore be detected and enumerated The sample may be such that larger NTA-detectable particles may progressively disappear and reduce in size through dissolution, dispersion or melting to become PCS measurable background material and which can therefore be detected and enumerated at stages throughout the process.

Two populations of PCS detectable reagents (e.g. proteins) may interact or react to form NTA detectable structures (e.g. by changes in size or enhancement or development of an optically detectable parameter such a fluorescence).

NTA detectable particles may be manipulated through the application of a motive force (electrical, magnetic, gravitational, etc.), especially to move in the presence of smaller background particles. Thus, for example, the particles may be analysed via NTA whilst undergoing electrophoresis in a user-applied electric field, or magnetophoresis in a user-applied magnetic field.

The NTA detectable particles may be motile.

The background particles may be caused to move, with the movement analysable by laser Doppler velocimetry, in a variant of DLS.

The difference in movement of the background particles and the larger contaminant particles may be measured.

PCS-measurable background changes in rheological nature due, for instance to gelling or melting, or due to chemically charges (e.g. pH) may result in modification of the behaviour of the larger, NTA-detectable particles. By monitoring the changes in the NTA-detectable particles, the changes in the background particles may be monitored.

The NTA particles modify the behaviour and nature of the PCS-detectable background particles.

The NTA-derived first information can be used, in real time to modify the capture (either temporally or spatially) of DLS/PCS second data.

In a second aspect, the invention provides apparatus for use in performing the method of the first aspect, the apparatus comprising:
- a light source means for producing a suitably focussed beam of radiation to illuminate a sample;
- a first detector system for obtaining the first information about the particles, using NTA;
- a second detector system for obtaining the second information about the particles, using dynamic light scattering; and
- data processing means programmed to determine the third information from the first information.

In a preferred embodiment, the data processing means will be further programmed to adjust the second information, using the third information, to produce fourth information, which represents adjusted information on the average size of particles in the sample.

Several different embodiments of the apparatus of the invention can be envisaged, and these include the following categories:
(a) spatially common and temporally common (i.e. the first and second detector systems are used to interrogate substantially the same part of the illuminated sample and at substantially the same time);
(b) spatially common, but temporally different (i.e. the first and second detector systems are used to interrogate substantially the same part of the illuminated sample but at substantially different times e.g. sequentially); and
(c) spatially different but temporally common (i.e. the first and second detector systems are used to interrogate different parts of the illuminated sample and substantially the same time).

There is a fourth category (d) in which the first and second detector systems are both spatially and temporally distinct, but such a category offers no significant advantages over categories (a)-(c) which are preferred.

Within category (a) apparatus, there are at least two sub-categories:
(e) in which both detector systems are angled with respect to one another to allow them to interrogate the same part of the illuminated sample, albeit from different angles—(this is not a difficulty, as long as the angle is known for the second detector system); or
(f) the light path from the sample is split, with one part passing to a CCD or the like for NTA, the other part passing to an APD or the like for DLS. It is implicit in this embodiment that the light path for both detector systems is, at least initially, common. For example, the light path may be split by a beam splitter located downstream of a common microscope objective lens. The split may be 50:50 between the two detector systems, but this is not essential.

It follows that, in some embodiments of the invention, at least, there may advantageously be one or more components, including, but not limited to, lenses and beam splitters, which are common to the first and second detector systems.

Apparatus of the invention under category (b) referred to above will involve the first and second detector systems interrogating substantially the same part of the sample but at different times. This will be acceptable, provided that the characteristics of the sample do not change in a significant way between the interrogation with the first detector system and interrogation with the second detection system. Typically the flow or ingress of sample into a sample chamber will be under computerised motor control, so this requirement can be met.

A potential disadvantage of apparatus under category (c) is that the first and second detector systems are interrogating different parts of the illuminated sample—to be reliable, not only must the sample be substantially homogenous, but the illumination must be substantially identical at the two locations in the sample being interrogated by the respective detector systems, and this may be harder to arrange, especially if the two locations are not very close together.

For the avoidance of doubt, it is hereby expressly stated that features described herein as "preferable", "desirable", "advantageous", "convenient" or the like may be present in the invention in isolation, or in any combination with any one or more other such features so described, unless the context dictates otherwise. In addition, features described as "preferable", "desirable", "advantageous" "convenient" or the like in relation to one aspect of the invention will be understood to be equally applicable to other aspects of the invention, unless the context dictates otherwise.

The invention will be further described, by way of illustration, in the following non-limiting Examples, and with reference to the accompanying drawings, in which.

Figure 1:
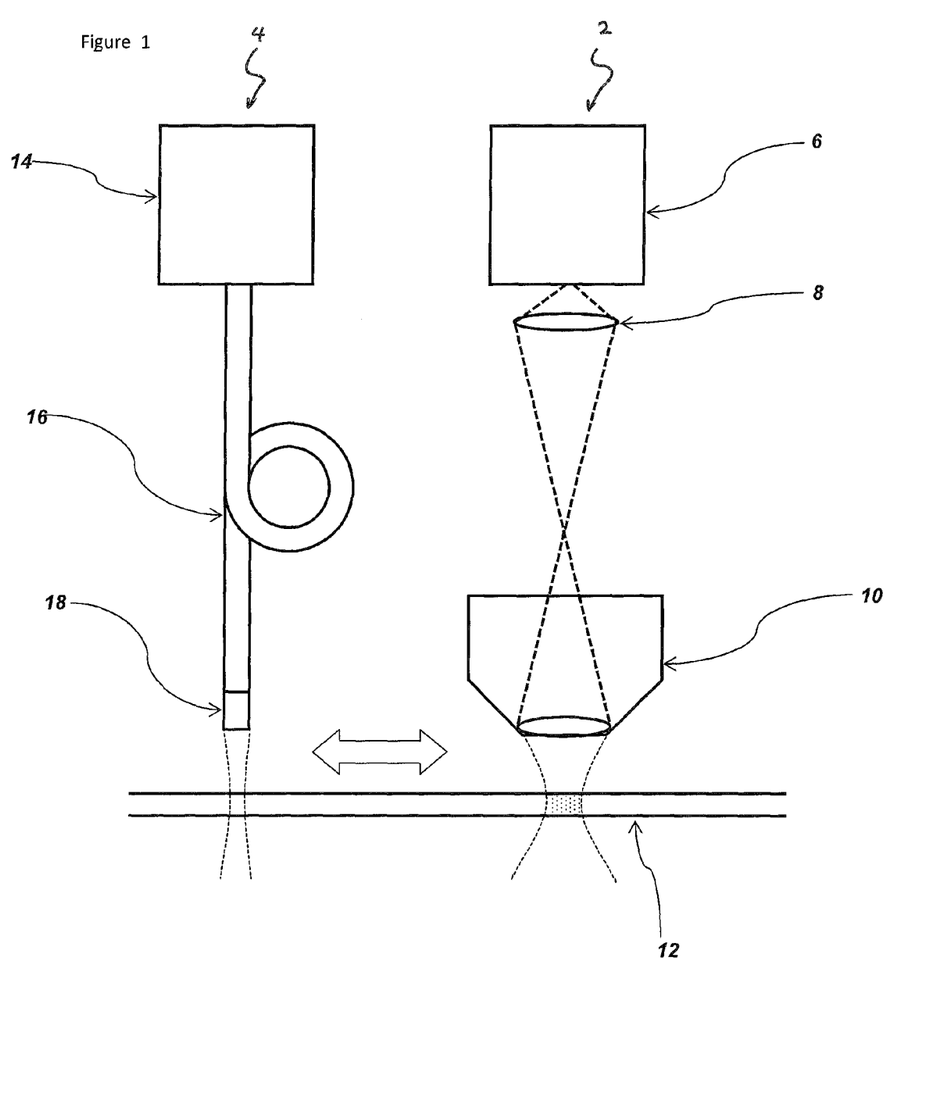
FIGS. 1-3 are schematic illustrations of different embodiments of apparatus suitable for performing the method of the invention.

Referring to FIG. 1, the diagram shows apparatus for performing NTA, indicated generally by reference numeral 2, and apparatus for performing DLS, indicated generally by reference numeral 4, the NTA apparatus 2 and DLS apparatus 4 being arranged to analyse a sample coincident in space or time (but not both). The NTA apparatus 2 comprises a CCD or EMCCD camera 6, lens 8, and a microscope objective lens 10, arranged to analyse a volume of sample illuminated by laser beam 12.

The DLS apparatus 4 comprises a photon counting detector 14, a fibre optic 16, and a microlens 18, arranged to analyse a volume or region of sample illuminated by the laser beam 12 either at the same time as NTA apparatus 2 is analysing a different volume or region of the sample, or analysing the same volume or region of sample as that analysed by the NTA apparatus but at a different time.

Figure 2:
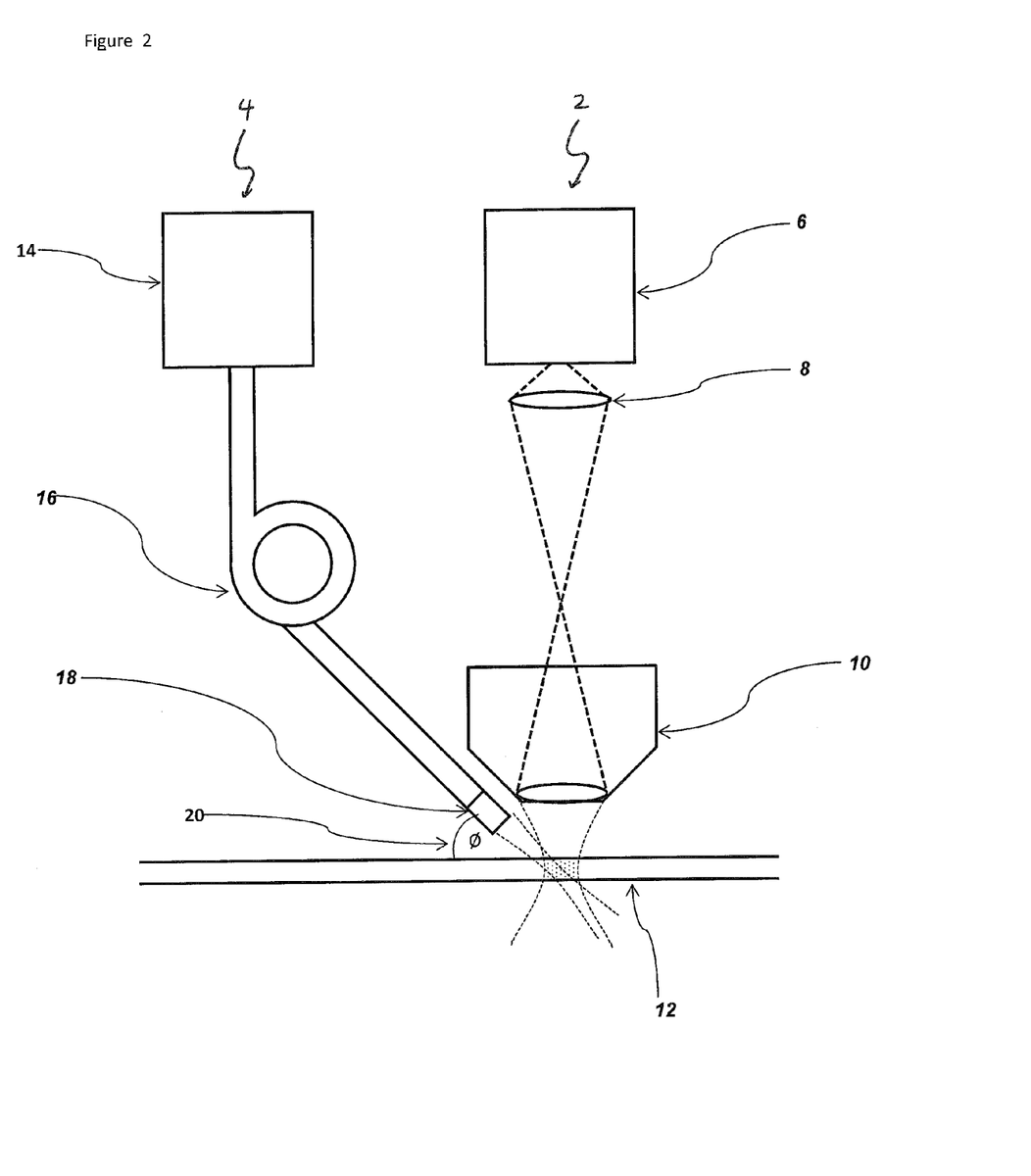

Referring to FIG. 2, the diagram schematically illustrates a second embodiment of apparatus for performing the method of the invention. Functionally equivalent components are denoted by the same reference numerals used in FIG. 1. The illustrated embodiment is a spatially and temporally common arrangement, in which the NTA apparatus 2 and DLS apparatus 4 are used to analyse the same volume or region of sample at the same time, but at different angles (the NTA apparatus being at right angles to the laser beam, the DLS apparatus being at angle theta, 20).

Figure 3:
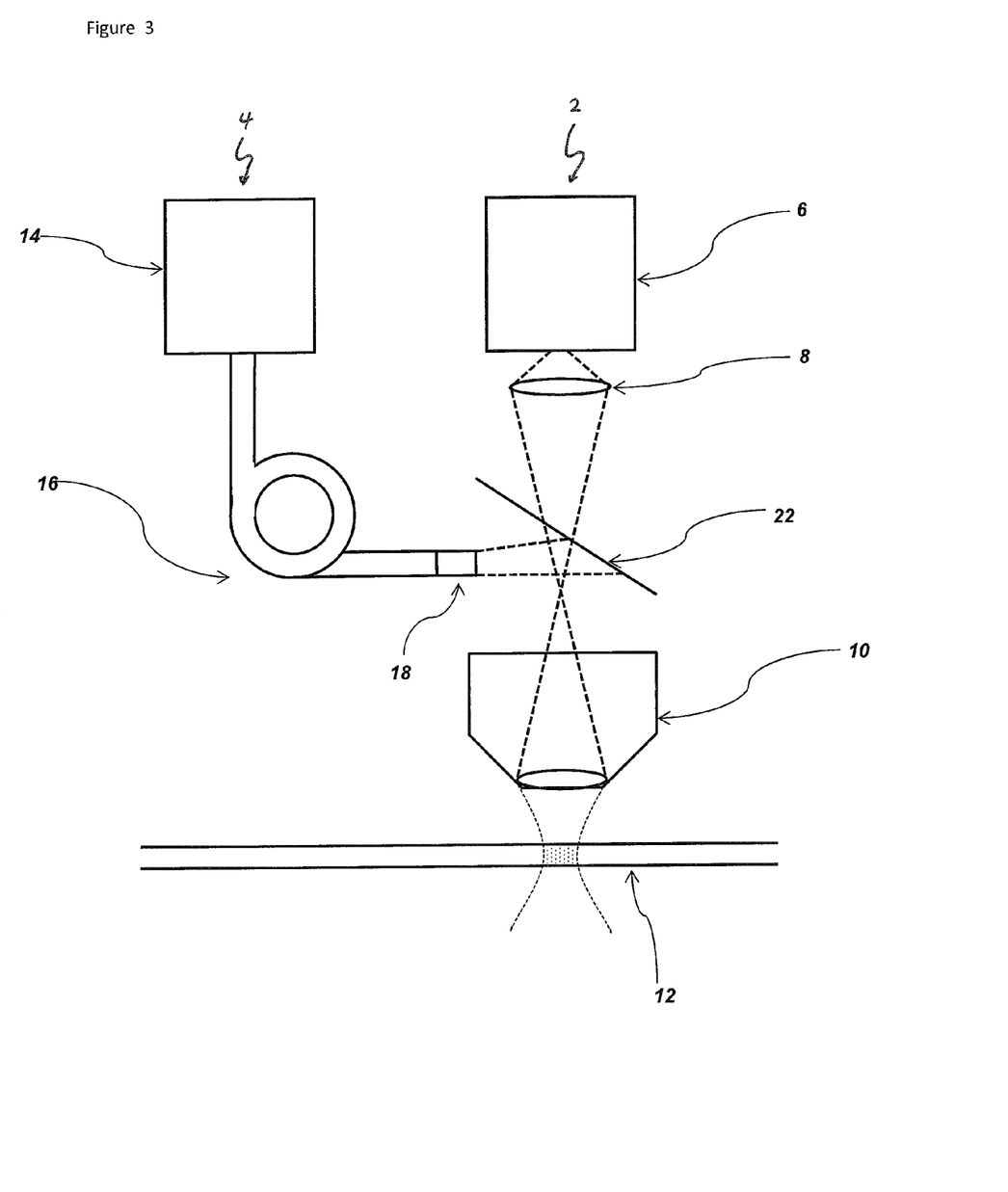

FIG. 3 illustrates schematically a third embodiment of apparatus for performing the method of the invention. Again, functionally equivalent components are denoted by the same reference numerals used in FIGS. 1 and 2. The illustrated embodiment is a spatially and temporally common arrangement, in which the NTA apparatus 2 and the DLS apparatus 4 are used to analyse the same volume or region of sample at the same time, and at the same angle (in contrast to the arrangement shown in FIG. 2), this being achieved by means of a beam splitter or dichroic mirror 22.

EXAMPLES

Example 1

In a typical embodiment, sample, e.g. a proteinaceous material (constituting relatively smaller, DLS-detectable particles) containing a statistically significant number of larger particles not detectable by DLS (e.g. contaminants or aggregates), is introduced into the path of the laser beam passing through a sample cell.

DLS Measurement—

Light scattered at a certain angle from particles present in a selected region of the illuminating laser beam (the measurement volume) is detected by a suitably configured detector and analysed by conventional DLS methodology as described above. The results are presented as a z-average (intensity weighted) mean of the population. In cases when the correlation function is analysed by a suitable de-convolution algorithm (e.g. Fourier transform), a particle size distribution profile may also be generated. The results are, respectively, either an intensity weighted mean of the population or a particle size distribution profile which is also intensity weighted to larger (e.g. contaminant) particles in the sample and limited in resolution by virtue of the ill-conditioned fit nature of the particle size distribution analysis. These results constitute the second information.

NTA Measurement—

Using a second detector system comprising a microscope objective and CCD camera, light scattered from the same measurement volume is analysed by NTA, preferably simultaneously. The results are presented as a direct number frequency particle size distribution profile of those particles sufficiently large to be individually identified and sized through analysis of their Brownian motion. These results constitute the first information. NTA will not, however, be able to report the presence, size or number of any monomeric nanoparticles which cannot be resolved as discrete light scattering centres, e.g. the unaggregated/contaminated proteinaceous background.

Merging the Two Data Sets—

The first and second information can now combined in the following way:

For each individual particle detected and sized by NTA, knowing the temperature, T, at which the size was obtained and the viscosity of the solvent, $\eta$, in which the particle was analysed at that temperature, it is possible to generate a theoretical second order autocorrelation curve, $g^2(\tau)$ that would have arisen from each particle radius, $r_h$, under DLS analysis.

For a single value of particle size (i.e. a single diffusion coefficient $D_t$), the resulting autocorrelation function describes an exponential.

$$g^2(\tau) = Ae^{-\Gamma\tau}$$

where $$\Gamma = q^2 D_t$$

Given, $$D_t = \frac{K_B T}{6\pi\eta r_h}$$

where $K_B$ is Boltzmann's constant and $$q = \frac{4\pi n_0}{\lambda} \sin\frac{\theta}{2}$$

where $n_o$ is solvent refractive index, $\lambda$ is wavelength and $\theta$ is the scattering angle, g is the first order autocorrelation function, $\tau$ is the sample time, A is the intercept, e is the exponent, q is the scattering vector and D is the diffusion coefficient.

For a sample containing a distribution of particle sizes as determined by NTA, the results are a distribution of sizes of individual particles each one of which can be used to generate a corresponding autocorrelation function which can all be summed to simulate the multi-exponential nature of a DLS measurement of such a distribution of particle sizes.

Of course, in DLS the multi-exponential autocorrelation function obtained is intensity weighted to those particles in the ensemble which scatter most light. For a meaningful correction of DLS data through incorporation of particle size information obtained by NTA, it is necessary to similarly weight the otherwise non-intensity weighted NTA data for each particle. Given each detected particle is separately measured by NTA, it is possible, through the application of Mie theory (see Kerker, M (1969), The Scattering of Light and Other Electromagnetic Radiation, Academic Press, and Bohren, C. F. and Huffman, D. R., (1983) Absorption and Scattering of Light by Small Particles, John Wiley and Sons, Inc.) to calculate the amount of light scattered by each particle as a function of its size but this calculation also requires a priori knowledge of the particle shape and its refractive index as well as that of the solvent, the wavelength, polarisation and intensity of illuminating light, light collection angle(s).

However, there is a more direct and simpler method to achieve the above. Given NTA measures both the size of a particle through analysis of its Brownian motion but can also measure the relative amount of light each particle is scattering by summing the grey-scale values from the CCD camera pixels imaging the spot of light scattered by each particle, it is possible to directly estimate the degree to which each NTA-detected particle would contribute to the overall signal detected by DLS, to generate the third information.

Thus, the NTA particle size number distribution plot can be intensity weighted on a particle-by-particle basis to give an intensity weighted Γ.

Given the intensity weighted NTA plot, I(Γ), for all sizes and number or particles measured, the summed theoretical second order autocorrelation curve, g² NTA(τ), is now given by;

$$g^2 NTA^{(\tau)} = \frac{1}{\int_0^\infty I(\Gamma)d\Gamma} \int_0^\infty I(\Gamma)e^{-2\Gamma\tau}d\Gamma$$

Adjusting the conventional DLS correlelogram (the second information) by correcting with the NTA-derived theoretical correlelogram (the third information) could be achieved, for example, by subtracting the latter from the former, the residuals being the 'contaminant compensated' DLS plot (the fourth information).

Different samples may contain different amounts of either non-NTA-resolvable PCS-measurable material (background haze) or PCS-contaminating, NTA-detectable particles (contaminants). By measuring the total amount of light scattered by the entire sample (both haze and contaminants) by summing the total grey-scale values from the entire CCD array imaging the sample measurement region and subtracting from this value the sum of all grey-scale values associated with discrete NTA-detected contaminants, it is possible to adjust the area under the NTA-modelled correlation curve compared to the area under the DLS correlation curve to recover information about the relative amounts of the two types of material present.

While the above method can be used to remove the effect of NTA-detectable particles from a DLS measurement, NTA can only detect particles down to a certain level (dependent on particle size and refractive index). For lower refractive index particles such as proteinaceous materials containing aggregates, this DLS-measurable but NTA-inaccessible region may cover, for instance, particles in the size range 5 nm to 50 nm (5 nm representing the primary protein molecule, 50 nm representing the largest of the non-NTA-detectable aggregates). This region may still, therefore, contain sub-50 nm protein aggregates but which cannot be NTA-compensated. This represents, therefore, a conventional intensity weight particle distribution which would suffer the same limitations as any other DLS measurement. This non-NTA-addressable region would therefore have to be analysed in terms of its multi-modality by one of the conventional PCS deconvolution algorithms such as CONTIN (see Provencher, Makromol. Chem. 180, 201 (1979); Provencher, Comput. Phys. Commun. 27, 213 (1982); and Provencher, Comput. Phys. Commun. 27, 229 (1982)) or NNLS (see Roig & Alessandrini 2006: "Particle Size Distributions from Static Light Scattering with Regularized Non-negative Least Squares Constraints" Part. Part. Syst. Charact. 23, 431-437)) or the like.

Other suitable techniques include: maximum entropy analysis (see Langowski & Bryan, "Maximum entropy analysis of photon correlation spectroscopy data using a Bayesian estimate for the regularization parameter", Macromolecules 1991, 24 (23), 6346-6348); maximum likelihood (see Sun & Walker: "Maximum Likelihood Data Conversion for photon correlation spectroscopy" Meas. Sci. Technol. 19); and exponential sampling (see Ostrowsky et al, "Exponential Sampling Method for Light Scattering Polydispersity Analysis", 1981 Optica Acta: Int. J. Optics 28(8)).

Example 2

Figure 4:
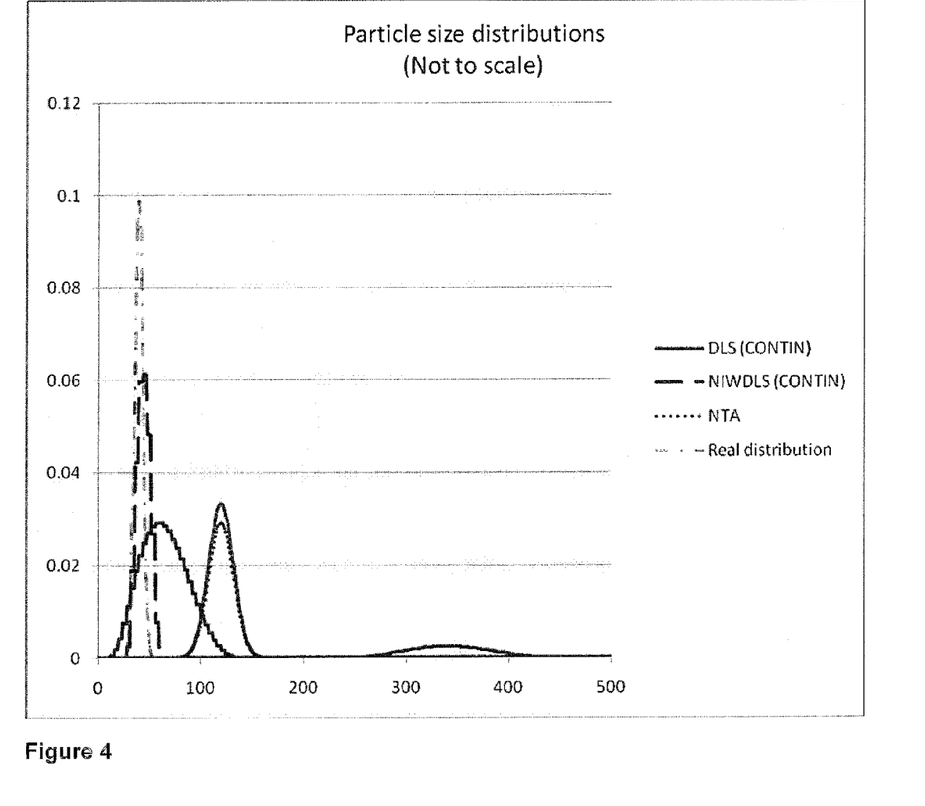
FIG. 4 is a graph of signal intensity (arbitary units) against particle diameter (nm) for a simulated sample of particles.

Example of the use of NIWDLS and NTA to recover accurate estimates of particle size distribution profiles in comparison to standard DLS A simulated sample comprising two particle populations of 40 nm and 120 nm diameter respectively (each exhibiting a 10% standard deviation in particle size distribution) were added together in a number ratio of 1000:1. FIG. 4 is a graph showing the particle size distributions (signal intensity, arbitrary units, against particle diameter, in nm). The "real distribution" is represented in FIG. 4 by the dash/dot/dash plot.

The NTA analysis of this mixture was calculated and is shown in FIG. 4 (dotted plot) in which the presence of the smaller 40 nm particles is not detected their being below the detection limit of NTA.

Figure 5:
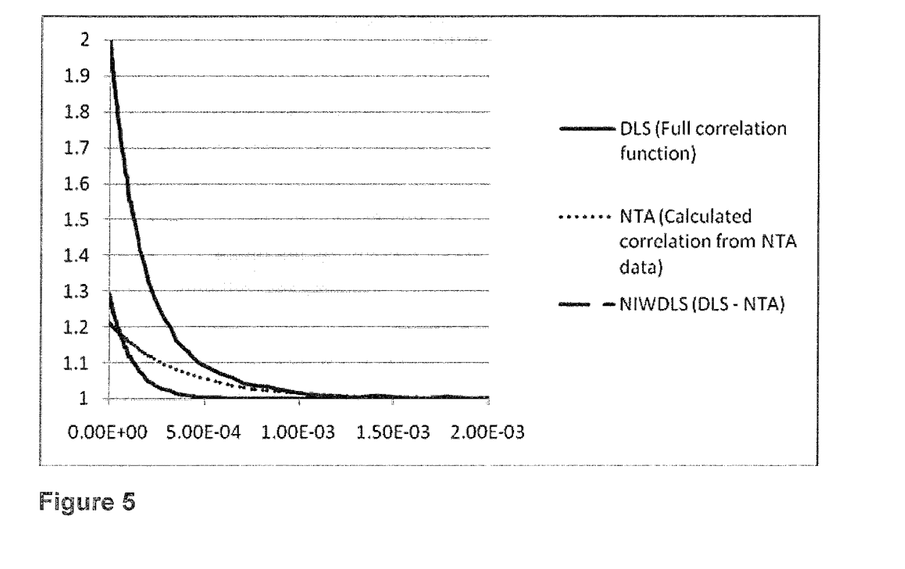
FIG. 5 is a graph showing different correlation functions described in Example 2.

Assuming a Rayleigh scattering relationship between size and scattered intensity, the number distribution was re-calculated as an intensity distribution as seen by dynamic light scattering and a correlogram consequently obtained (solid line, FIG. 5). When subject to analysis by CONTIN (a deconvolution algorithm for the calculation of particle size distributions from DLS correlation functions) the resulting profile (solid plot, FIG. 4) exhibits the intensity weighted profile typically obtained under DLS in which the mixture is portrayed as essentially a single peak lying between the actual peaks (DLS being incapable of resolving bimodal mixtures as close a 40 and 120 nm) with some noise out at 300-400 nm. Note that the presence of a bimodal distribution is missed in conventional DLS at these number ratios.

Using the profile of the detectable 120 nm particles obtained by NTA, a correlation function was calculated (dotted line, FIG. 5) and subtracted from the 'real' DLS correlation function. The resulting curve ("NIWDLS (DLS-NTA)" dashed plot, FIG. 5) was subject to CONTIN particle size distribution analysis and re-plotted (dashed line FIG. 4), NIWDLS (CONTIN)).

As can be seen in FIG. 4, the real distribution (dash-dot-dash) is mistakenly measured by DLS as an incorrect profile of the wrong size (solid plot). NTA is capable of accurately determining the true size of the 'NTA-visible' 120 nm particles but cannot detect the smaller 40 nm particles because they are too small to see on an individual basis. However, by back-calculating the correlation function that would have been obtained from particles of such size and distribution width and subtracting this from the correlation function obtained by DLS, it is possible to obtain a correlation function and consequent CONTIN profile (or any other suitable de-convolution algorithm) from which the effect of intensity weighting has been removed. This Non-Intensity Weighted Dynamic Light Scattering (NIWDLS) profile (dashed line FIG. 4) can be combined with the NTA profile (dotted line FIG. 4) to reflect accurately the true nanoparticle population (dash-dot line FIG. 4). This simplistic approach of subtracting the estimated correlation function could be substituted for a suitable modification to a given de-convolution algorithm (including but not limited to CONTIN, maximum entropy, maximum likelihood, exponential sampling, NNLS) to take the NTA distribution and estimated correlation function as prior information, along with the DLS correlation function.

The invention claimed is:

1. A method of analysing a sample comprising a polydisperse population of sub-micron particles, said sample comprising a plurality of small particles, and a plurality of large nanoparticle tracking analysis (NTA)-detectable particles, the method comprising: determining first information about the size and number of the NTA-detectable particles in the sample by NTA; determining second information about average particle size of all the particles in the sample by dynamic light scattering ("DLS data"); using the first information to produce third information comprising the predicted effect of the NTA-detectable particles on the results obtained by dynamic light scattering; and using the third information to compensate for the predicted effect of the NTA-detectable particles on the DLS data to produce fourth information representing corrected information on average particle size.

2. The method according to claim 1, wherein the first and second information are obtained simultaneously from the same sample.

3. The method according to claim 1, wherein the sample comprises a suspension or other dispersion of solid particles in liquid.

4. The method according to claim 1, wherein the sample is illuminated by a focused beam of radiation.

5. The method according to claim 1, wherein the first information further includes information on particle brightness/spectral characteristics.

6. The method according to claim 1, wherein the second information also further includes information on particle size distribution.

7. The method according to claim 1, wherein the first information and the second information are obtained using respective detector systems.

8. The method according to claim 1, wherein the first information is used to generate a theoretical correlation curve or function for one or more of the detected particle sizes.

9. The method according to claim 8, wherein the correlation function is size-weighted, with larger particles being given greater weighting.

10. The method according to claim 8, wherein correlation functions for different particle sizes are summed.

11. The method according to claim 1, wherein the first information includes information on the relative amount of light scattered by each detected particle.

12. The method according to claim 1, wherein the sample comprises proteins.

13. The method according to claim 1, wherein the sample comprises particles which are fluorescent.

14. The method according to claim 1, wherein the first or second information is obtained whilst the particles are subjected to a user-applied external electric or magnetic field.

15. An apparatus adapted and configured for performing the method of claim 1, the apparatus comprising:
a light source producing a focused beam of radiation to illuminate the sample;
a first detector system for obtaining the first information using nanoparticle tracking analysis (NTA);
a second detector system for obtaining the second information using dynamic light scattering; and
data processing means programmed to determine the third information from the first information.

16. The apparatus according to claim 15, wherein the data processing means is further programmed to adjust the second information, using the third information, to produce the fourth information.

17. The apparatus according to claim 15, wherein the first and second detector systems are spatially common and temporally common.

18. The apparatus according to claim 15, wherein the first and second detector systems are spatially common but temporally different.

19. The apparatus according to claim 15, wherein the first and second detector systems are spatially different but temporally common.

20. The apparatus according to claim 15, wherein there are one or more components which are common to the first and second detector systems.

* * * * *